(12) United States Patent
Zhang et al.

(10) Patent No.: US 8,176,914 B2
(45) Date of Patent: May 15, 2012

(54) ANESTHETIC ABSORBING CIRCLE

(75) Inventors: Hongyu Zhang, Beijing (CN); Feng Guo, Beijing (CN); Xueli Xu, Beijing (CN)

(73) Assignee: Beijing Aeonmed Co., Ltd., Beijing (CN)

( * ) Notice: Subject to any disclaimer, the term of this patent is extended or adjusted under 35 U.S.C. 154(b) by 726 days.

(21) Appl. No.: 12/344,487

(22) Filed: Dec. 27, 2008

(65) Prior Publication Data

US 2009/0165785 A1 Jul. 2, 2009

(30) Foreign Application Priority Data

Dec. 29, 2007 (CN) .......................... 2007 1 0308324

(51) Int. Cl.
*A61M 16/12* (2006.01)
(52) U.S. Cl. ............................... 128/203.12; 128/205.11
(58) Field of Classification Search ............. 128/205.28, 128/204.18, 205.12, 205.27, 203.12, 205.11
See application file for complete search history.

(56) References Cited

U.S. PATENT DOCUMENTS

| | | | | |
|---|---|---|---|---|
| 3,910,261 A * | 10/1975 | Ragsdale et al. | ............... | 600/532 |
| 4,150,670 A * | 4/1979 | Jewett et al. | ............. | 128/204.22 |
| 4,596,246 A * | 6/1986 | Lyall | ........................ | 128/202.27 |
| 5,231,980 A * | 8/1993 | Filipovic et al. | ......... | 128/205.12 |
| 5,471,979 A * | 12/1995 | Psaros et al. | ............. | 128/205.28 |
| 5,515,845 A * | 5/1996 | Filipovic et al. | ......... | 128/205.12 |
| 5,694,924 A * | 12/1997 | Cewers | ..................... | 128/204.21 |
| 5,701,888 A * | 12/1997 | Tham et al. | .............. | 128/204.21 |
| 5,979,443 A * | 11/1999 | Dingley | ..................... | 128/204.28 |
| 6,125,848 A * | 10/2000 | Hendrickson et al. | ... | 128/204.22 |
| 6,523,537 B1 * | 2/2003 | Mas Marfany | .......... | 128/203.12 |
| 6,622,725 B1 * | 9/2003 | Fisher et al. | ............. | 128/204.21 |
| 7,938,111 B2 * | 5/2011 | Lischinski | ................ | 128/202.27 |
| 7,987,849 B2 * | 8/2011 | Heesch | ..................... | 128/205.28 |
| 2008/0190431 A1 * | 8/2008 | Bellefeuille | .............. | 128/205.24 |
| 2008/0264414 A1 * | 10/2008 | McNeilly et al. | ......... | 128/203.12 |
| 2008/0289628 A1 * | 11/2008 | Hallback et al. | .......... | 128/203.12 |
| 2009/0250054 A1 * | 10/2009 | Loncar et al. | ............. | 128/203.14 |
| 2009/0277448 A1 * | 11/2009 | Ahlmen et al. | ........... | 128/204.21 |
| 2011/0061650 A1 * | 3/2011 | Heesch | ..................... | 128/203.12 |
| 2011/0168177 A1 * | 7/2011 | Connor | ..................... | 128/203.14 |

* cited by examiner

*Primary Examiner* — Stephen Crow
(74) *Attorney, Agent, or Firm* — Sawyer Law Group, P.C.

(57) ABSTRACT

The present invention relates to an anesthetic absorbing circle, comprising: a first common tube, providing an anesthetic gas mixture; an inspiration branch, connected to the first common tube and delivering the anesthetic gas mixture to a patient end; an expiration branch, connected to the first common tube and sending back the expired gas from the patient end to the first common tube; a second common tube, connected with the inspiration branch and the expiration branch at its first end and connected with the patient end at its second end; and a flow sensor, wherein the flow sensor is disposed in the first common tube. Thus, according to the present invention, the flow sensor can conduct bidirectional monitoring, the flow sensor is remote from patients, and water accumulation at the probe will not appear; in addition, the probe can be easily detached and disinfected at a high temperature, and can be used between adults and children.

9 Claims, 1 Drawing Sheet

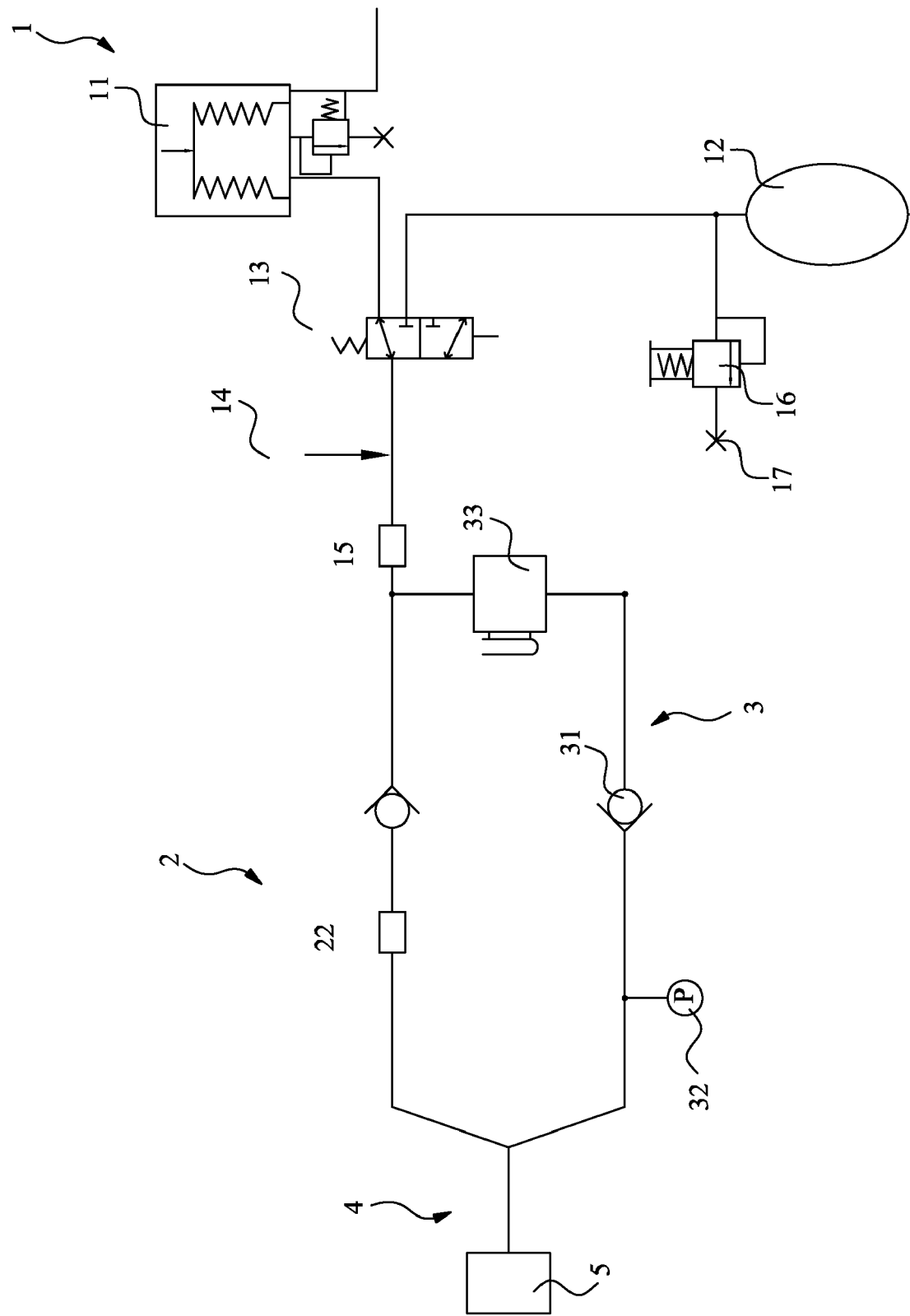

ANESTHETIC ABSORBING CIRCLE

Under 35 USC §120, this application claims the benefit of priority to CHINA Patent Application No. 200710308324.1, filed Dec. 29, 2007 entitled "ANESTHETIC ABSORBING CIRCLE", all of which is incorporated herein by reference.

FIELD OF THE INVENTION

The present invention relates to an anesthetic absorbing circle, and in particular, a closed anesthetic absorbing circle.

BACKGROUND

In the field of anesthetic machine for medical treatment, where multiple anesthetic absorbing circles are raised, e.g., a multifunctional anesthetic machine for medical treatment is composed of an expiration tube, an inspiration tube, a gas storage pocket, a fast oxygen supply switch, an inspiring switch, a dropper, a carbon dioxide absorber, a circle internal-external change-over switch, and a multifunctional volatilizer with corresponding connection tubes. The circle internal-external change-over switch may select the anesthetic machine to operate in in-circle mode or out-circle mode. The multifunctional volatilizer has multifunctional volatilizing manners. The multifunctional anesthetic machine has a plurality of functions, and has advantages of small volume, low weight and low cost, especially rescue and field application.

In addition, there is a low flux anesthetic circle in the art. The anesthetic circle is characterized in that an expiratory valve is connected in series to an expiration valve, an inspiration combination valve is mounted between two $CO_2$ absorbers, a common gas inlet 4 is located at the lower portion of a one-way valve in the combination valve, and a gas storage pocket is used as a buffer gas pocket, etc. Thus, the concentration of the inspired anesthetic gas can be changed rapidly by way of changing the concentration of the anesthetic gas of the common gas, and the tidal volume of a respiration machine will not be affected by the flux of the common gas of the anesthetic respiration machine. Above all, the anesthetic circle is especially applicable for low flux or extremely low flux anesthetic in clinic.

However, neither of the above two anesthetic circles allows for the monitoring of the flux in the circle.

At the present time, in order to monitor and control the anesthetic gas delivered to the patient, a flow sensor is mounted in an anesthetic absorbing circle of the anesthetic machine; the flow sensor is generally located at an inspiration end, an expiration end (called unidirectional monitoring) and a patient end after a Y-shaped triple tube (called bidirectional detection) of the anesthetic absorbing circle. A unidirectional flow sensor can monitor only the conditions of the flux and the pressure of inspiration or expiration; the flow sensor for the patient end after the Y-shaped triple tube can monitor the conditions of the flux and the pressure of the inspiration or expiration, but such arrangement will increase dead space, makes the sensor disconnected easily, has water accumulation at the probe and operates inconveniently.

Accordingly, what is needed is a system and method that addresses the above identified issues. The present invention addresses such a need.

SUMMARY OF THE INVENTION

A system and method in accordance with an embodiment provides an anesthetic absorbing circle which conducts bidirectional monitoring with one probe, avoids the disconnection of the bidirectional monitoring flow sensor of the patient end, prevents the water accumulation at the probe and operates conveniently.

In order to achieve the above, a system and method in accordance with an embodiment provides an anesthetic absorbing circle, comprising: a first common tube, providing an anesthetic gas mixture; an inspiration branch, connected to the first common tube and delivering the anesthetic gas mixture to a patient end; an expiration branch, connected to the first common tube and sending back the expired gas from the patient end to the first common tube; a second common tube connected with the inspiration branch and the expiration branch at its first end and connected with the patient end at its second end; and a flow sensor, wherein the flow sensor is disposed in the first common tube.

According to an embodiment, a wind box automatically provides an anesthetic gas, a gas storage pocket manually providing an anesthetic gas, and a mechanical/manual change-over switch switching between the wind box and the gas storage pocket are disposed in the first common tube.

According to an embodiment, a fresh air inlet is further disposed in the first common tube for providing fresh air so as to be mixed with the anesthetic gas to form a gas mixture.

According to an embodiment, an adjustable pressure limiting (APL) valve and a gas exhaust orifice is further disposed in the first common tube, wherein the pressure in the first common tube is adjusted by adjusting the APL valve and the exhaustion of the gas from the gas exhaust orifice.

According to an embodiment, an inspiration valve is disposed in the inspiration branch for unidirectionally allowing the gas mixture inspired by the patient end to pass.

According to an embodiment, an oxygen concentration sensor is disposed in the inspiration branch, for detecting the oxygen concentration in the gas mixture reaching the patient end.

According to an embodiment, an expiration valve is disposed in the expiration branch, for unidirectionally allowing the gas mixture expired from the patient end to pass.

According to an embodiment, a pressure gauge is further disposed in the expiration branch, for detecting the pressure in the gas mixture expired from the patient end.

According to the present invention, a carbon dioxide absorber is further disposed in the inspiration branch, for absorbing the carbon dioxide in the gas mixture.

Wherein, when the mechanical/manual change-over switch is set in mechanical-control mode, the mixed fresh gas in the wind box (when the mechanical/manual change-over switch is set in a manual mode, the anesthetic gas is sent out from the gas storage pocket) is delivered to a patient via the flow sensor, the inspiration valve, and the oxygen concentration sensor, when the patient inspires. The gas expired from the patient is then sent to the wind box (when the mechanical/manual change-over switch is set in the manual mode, the anesthetic gas is sent back to the air storage pocket) via the pressure gauge, the expiration valve, the carbon dioxide absorber, and the flow sensor. Thus the flow sensor can monitor the flux of the gas inspired and expired by the patient end.

The advantageous effects of the technical solution lie in that the flow sensor can conduct bidirectional detection, the flow sensor is remote from patients, and the water accumulation at the probe will not appear. In addition, the probe can be easily detached and disinfected at a high temperature, and can be used by both adults and children.

BRIEF DESCRIPTION OF THE DRAWINGS

The purpose, advantages and features of the present invention will become more apparent by description with reference to the following accompanying drawing.

FIG. 1 is a schematic view showing the principle of operation of an embodiment of an anesthetic absorbing circle.

DETAILED DESCRIPTION OF THE INVENTION

The present invention will be described in detail with reference to the accompanying drawing.

The present invention relates to an anesthetic absorbing circle, and in particular, a closed anesthetic absorbing circle. The method and system have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

FIG. 1 is a schematic view showing the principle of the operation of an embodiment of an anesthetic absorbing circle. FIG. 1 shows an anesthetic absorbing circle, comprising: a first common tube 1, providing a gas mixture; an inspiration branch 2, connected to the first common tube 1 and for delivering the anesthetic mixture gas to a patient end 5. The absorbing circle includes an expiration branch 3 connected to the first common tube 1 for sending back the expired gas from the patient end 5 to the first common tube 1 and a second common tube 4 connected with the inspiration branch 2. The expiration branch 3 at its first end is connected with the patient end 5 and at its second end is connected with common tube 1. The absorbing circle includes a flow sensor 15, wherein the flow sensor 15 is disposed in the first common tube 1.

A wind box 11, a gas storage pocket 12, a mechanical/manual change-over switch 13, a fresh air inlet 14, an APL valve 16 and a gas exhaust orifice 17 are disposed in the first common tube 1. The wind box 11 and the gas storage pocket 12 provide anesthetic gas automatically to a patient end 5 or manually via the mechanical/manual change-over switch 13. The fresh air inlet 14 provides fresh air, which is mixed with the anesthetic gas to form a gas mixture. The flow sensor 15 is in communication with the fresh air inlet 14 and the out port of the mechanical/manual change-over switch 13, for detecting the flux of the gas mixture when the gas is provided automatically or manually. The flow sensor 15 is also in communication with an expiration valve 31, a pressure gauge 32 and a carbon dioxide absorber 33, for detecting the flux of the gas mixture expired from the patient end 5. In addition, the pressure in the first tube 1 can be adjusted by an adjustable pressure limiting (APL) valve 16 and the gas exhaust orifice 17.

According to an embodiment, an inspiration valve 21 and an oxygen concentration sensor 22 are disposed in the inspiration branch 2. The inspiration valve 21 only allows the patient end 5 to inspire the gas mixture unidirectionally, and the oxygen concentration sensor 22 is used to detect the oxygen concentration in the gas mixture reaching the patient end 5.

According to an embodiment, an expiration valve 31, a pressure gauge 32 and a carbon dioxide absorber 33 are disposed in the expiration branch 3. The expiration valve 31 only allows the patient end to expire the gas mixture unidirectionally. The pressure gauge 32 is used to detect the pressure in the gas mixture expired from the patient end 5. The carbon dioxide absorber 33 can be used to absorb carbon dioxide in the gas mixture.

According to an embodiment, when the mechanical/manual change-over switch is in mechanical-control mode, the mixed fresh gas in the wind box (when the mechanical/manual change-over switch is in a manual mode, the anesthetic is sent out from the gas storage pocket) is delivered to a patient via the flow sensor, the inspiration valve, and the oxygen concentration sensor, as the patient inspires. The gas expired from the patient is sent to the wind box (when the mechanical/manual change-over switch is in the manual one, the anesthetic gas is sent back to the air storage pocket) via the pressure gauge, the expiration valve, the carbon dioxide absorber, and the flow sensor, so that the flow sensor can detect the flux of the gas inspired and expired by the patient end.

According to an embodiment, the flow sensor can conduct bidirectional detection and is also remote from patients, and the water accumulation at the probe will not appear. In addition, the probe can be easily detached and disinfected at a high temperature, and can be used by both adults and children.

It should be understood by those of ordinary skill in the art that various replacements, modifications and changes in the form and details may be made therein without departing from the spirit and scope of the present invention as defined by the following claims. Therefore, it is to be appreciated that the above described embodiments are for purposes of illustration only and are not to be construed as being limitations of the present invention.

What is claimed is:

1. An anesthetic absorbing circle, comprising:
a first common tube (1), providing an anesthetic gas mixture;
an inspiration branch (2), connected at the first end thereof to the first common tube (1) and delivering the anesthetic gas mixture to a patient end (5);
an expiration branch (3), connected at the first end thereof to the first common tube (1) and sending back the expired gas from the patient end (5) to the first common tube (1);
a second common tube (4), wherein the first end of the second common tube is connected to the second end of the inspiration branch (2) and the second end of the expiration branch (3) respectively, and the second end of the second common tube is connected to the patient end (5); and
a flow sensor(15), wherein the flow sensor (15) is disposed in the first common tube (1).

2. The anesthetic absorbing circle according to claim 1, wherein a wind box (11), a gas storage pocket (12) and a mechanical/manual change-over switch (13) are disposed in the first common tube (1), wherein the wind box (11) is automatically operable to provide an anesthetic gas, the gas storage pocket (12) is manually operatable to provide an anesthetic gas, and the mechanical/manual change-over switch (13) switches between the wind box and the gas storage pocket so as to selectively communicate with the wind box (11) or the gas storage pocket (12).

3. The anesthetic absorbing circle according to claim 2, wherein a fresh air inlet (14) is disposed in the first common tube (1) for providing fresh air so as to be mixed with the anesthetic gas provided by the wind box (11) or the gas storage pocket (12) via the mechanical/manual switch (13) to form a gas mixture.

4. The anesthetic absorbing circle according to claim 2, wherein an APL valve (16) and an air exhaust orifice (17) are further disposed in the first common tube (1), wherein the pressure in the first common tube (1) is adjusted by adjusting the APL valve (16) so as to exhaust the gas in the first common tube (1) via the gas exhaust orifice (17).

5. The anesthetic absorbing circle according to claim 1, wherein an inspiration valve (21) is disposed in the inspiration branch (2) for unidirectionally allowing the gas mixture inspired by the patient end to pass.

6. The anesthetic absorbing circle according to claim 5, wherein an oxygen concentration sensor (22) is disposed in the inspiration branch (2) for detecting the oxygen concentration in the gas mixture reaching the patient end (5).

7. The anesthetic absorbing circle according to claim 1, characterized in that an expiration valve (31) is disposed in the expiration branch (3) for unidirectionally allowing the gas mixture expired from the patient end (5) to pass.

8. The anesthetic absorbing circle according to claim 7, wherein a pressure gauge (32) is disposed in the expiration branch (3) for detecting the pressure in the gas mixture expired from the patient end (5).

9. The anesthetic absorbing circle according to claim 7, wherein a carbon dioxide absorber (33) is further disposed in the inspiration branch (3) for absorbing carbon dioxide in the gas mixture.

\* \* \* \* \*